United States Patent
McDonell et al.

(10) Patent No.: US 9,730,835 B2
(45) Date of Patent: Aug. 15, 2017

(54) BURST MODE VITRECTOMY SYSTEM

(71) Applicant: Novartis AG, Basel (CH)

(72) Inventors: Brian William McDonell, Irvine, CA (US); Venkatesh Vasudevan, Beachwood, OH (US)

(73) Assignee: Novartis AG, Basel (CH)

( * ) Notice: Subject to any disclaimer, the term of this patent is extended or adjusted under 35 U.S.C. 154(b) by 187 days.

(21) Appl. No.: 14/096,072

(22) Filed: Dec. 4, 2013

(65) Prior Publication Data
US 2014/0171996 A1   Jun. 19, 2014

Related U.S. Application Data

(60) Provisional application No. 61/739,338, filed on Dec. 19, 2012.

(51) Int. Cl.
*A61B 17/32*    (2006.01)
*A61F 9/007*    (2006.01)

(52) U.S. Cl.
CPC ................ *A61F 9/00763* (2013.01)

(58) Field of Classification Search
CPC .............. A61F 9/00763; A61F 9/00754; A61F 9/00745; A61F 9/00736
See application file for complete search history.

(56) References Cited

U.S. PATENT DOCUMENTS

| | | | |
|---|---|---|---|
| 5,257,988 A | 11/1993 | L'Esperance | |
| 6,773,445 B2 | 8/2004 | Finlay et al. | |
| 6,780,165 B2 | 8/2004 | Kadziauskas et al. | |
| 6,939,317 B2 | 9/2005 | Zacharias | |
| 7,600,405 B2 | 10/2009 | Maurer, Jr. et al. | |
| 7,824,870 B2 | 11/2010 | Kovalcheck et al. | |
| 7,846,126 B2 | 12/2010 | Steen et al. | |
| 7,938,120 B2 | 5/2011 | Kadziauskas et al. | |
| 7,945,341 B2 | 5/2011 | Boukhny et al. | |
| 8,048,094 B2 | 11/2011 | Finlay et al. | |
| 8,172,865 B2 | 5/2012 | DeBoer et al. | |
| 8,298,253 B2 | 10/2012 | Charles | |
| 8,312,800 B2 | 11/2012 | Turner et al. | |
| 9,119,700 B2 | 9/2015 | Boukhny | |
| 2007/0078379 A1 | 4/2007 | Boukhny et al. | |
| 2012/0302941 A1* | 11/2012 | Teodorescu ......... | A61F 9/00745 604/22 |
| 2014/0171994 A1* | 6/2014 | Lee .................... | A61F 9/00763 606/170 |
| 2014/0296900 A1 | 10/2014 | Barnes et al. | |

FOREIGN PATENT DOCUMENTS

WO   WO 2014/099982 A1   6/2014
WO   WO 2014/099993 A1   6/2014

OTHER PUBLICATIONS

Brian William McDonell "Dual Mode Vitrectomy Surgical Systems" U.S. Appl. No. 14/534,361, filed Nov. 6, 2014, 44 pages.

* cited by examiner

*Primary Examiner* — Ashley Fishback

(57) ABSTRACT

A vitrectomy surgical system includes a vitrectomy probe having a cutting portion comprising an inner tube, an outer tube, and an aspiration port. The inner tube may be movable relative to the outer tube to cut vitreous fibers. The system also includes a controller associated with the vitrectomy probe and configured to control movement of the inner tube by generating control signals corresponding to a cutting scheme including a plurality of series of cuts with each cut being evenly spaced in time, the plurality of series of cuts separated by a recovery period.

10 Claims, 8 Drawing Sheets

BURST MODE VITRECTOMY SYSTEM

PRIORITY CLAIM

This application claims the benefit of priority of U.S. Provisional Patent Application Ser. No. 61/739,338 titled "BURST MODE VITRECTOMY SYSTEM," filed on Dec. 19, 2012, whose inventors are Brian William McDonell and Venkatesh Vasudevan, which is hereby incorporated by reference in its entirety as though fully and completely set forth herein.

BACKGROUND

The present invention pertains to vitrectomy probes, systems, and methods. More particularly, but not by way of limitation, the present invention pertains to control of vitrectomy probes, systems, and methods.

Microsurgical procedures frequently require precision cutting and/or removing various body tissues. For example, certain ophthalmic surgical procedures require cutting and removing portions of the vitreous humor, a transparent jelly-like material that fills the posterior segment of the eye. The vitreous humor, or vitreous, is composed of numerous microscopic fibrils that are often attached to the retina. Therefore, cutting and removing the vitreous must be done with great care to avoid traction on the retina, the separation of the retina from the choroid, a retinal tear, or, in the worst case, cutting and removal of the retina itself. In particular, delicate operations such as mobile tissue management (e.g. cutting and removal of vitreous near a detached portion of the retina or a retinal tear), vitreous base dissection, and cutting and removal of membranes are particularly difficult.

The use of microsurgical cutting probes in posterior segment ophthalmic surgery is well known. These cutting probes typically include a hollow outer cutting member, a hollow inner cutting member arranged coaxially with and movably disposed within the hollow outer cutting member, and a port extending radially through the outer cutting member near the distal end thereof. Vitreous humor and/or membranes are aspirated into the open port, and the inner member is actuated, closing the port. Upon the closing of the port, cutting surfaces on both the inner and outer cutting members cooperate to cut the vitreous and/or membranes, and the cut tissue is then aspirated away through the inner cutting member.

One complication arising during vitrectomy procedures is retinal traction. High traction forces may lead to complications such as retinal tears and retinal detachments. One method that has been used to reduce vitreous traction is the use of increased cut rates. While utilizing these higher cut rates has reduced the average and peak traction, it appears that between cuts the residual traction remains higher than at lower cut rates. It is believed that this is due to the reduction of port closed time between cuts that has occurred with higher cut rates. With the very short time that the port is closed between cuts, the vitreous fibrils do not have a chance to retract and withdraw from the field of influence at the port.

The present disclosure is directed to addressing one or more of the deficiencies in the prior art.

SUMMARY

In an exemplary aspect, the present disclosure is directed to a vitrectomy surgical system that includes a vitrectomy probe having a cutting portion comprising an inner tube, an outer tube, and an aspiration port. The inner tube may be movable relative to the outer tube to cut vitreous fibers. The system also includes a controller associated with the vitrectomy probe and configured to control movement of the inner tube by generating control signals corresponding to a cutting scheme including a plurality of series of cuts with each cut being evenly spaced in time, the plurality of series of cuts separated by a recovery period.

In some aspects, the recovery period is a period of time equal to or greater than a single cutting cycle of one of the plurality of series of cuts. In an aspect, the system is selectively operated in a burst mode and a continuous mode, wherein when operating in the continuous mode, the controller is configured to generate control signals corresponding to a cutting scheme including a series of cuts evenly spaced in time that are not separated by a recovery period. In an aspect, the system includes a valve controlling fluid flow to the vitrectomy probe, the valve being controlled by said control signals generated by the controller. In an aspect, the system includes an input switch operable by a user and configured to switch the mode from continuous mode to burst mode. In an aspect, the controller is configured to initiate a recovery period based on passage of time. In an aspect, the controller is configured to insert a recovery period based on the number of cuts in a series.

In another exemplary aspect, the present disclosure is directed to a vitrectomy surgical system that includes a vitrectomy probe having a cutting portion comprising an inner tube and an outer tube. The inner tube may be movable relative to the outer tube to cut vitreous fibers. The system includes an actuator that controls the inner tube movement relative to the outer tube of the vitrectomy probe, and may include a controller that communicates control signals and that selectively operates in a continuous mode and in a burst mode. When in the continuous mode, the controller may control movement of the inner tube by generating control signals corresponding to a first cutting scheme including a series of cuts with each cut being evenly spaced in time. When in the burst mode, the controller may control movement of the inner tube by generating control signals corresponding to a second cutting scheme including a plurality of series of cuts with each cut being evenly spaced in time, the plurality of series of cuts separated by a recovery period.

In another exemplary aspect, the present disclosure is directed to a method including receiving an input from a user to generate control signals to initiate a cutting action with a vitrectomy probe; and generating control signals corresponding to a cutting scheme including a plurality of series of cuts with each cut being evenly spaced in time, the plurality of series of cuts separated by a recovery period.

In an aspect, the method includes opening and closing a valve in accordance with the control signals to initiate the cutting with the vitrectomy probe. In an aspect, the method includes selectively generating control signals corresponding to a second cutting scheme including a continuous series of cuts with each cut being evenly spaced in time. In an aspect, generating the control signals includes initiating a recovery period after a set number of cuts in a series.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTION OF THE DRAWINGS

The accompanying drawings illustrate embodiments of the devices and methods disclosed herein and together with the description, serve to explain the principles of the present disclosure.

DETAILED DESCRIPTION

Figure 1:
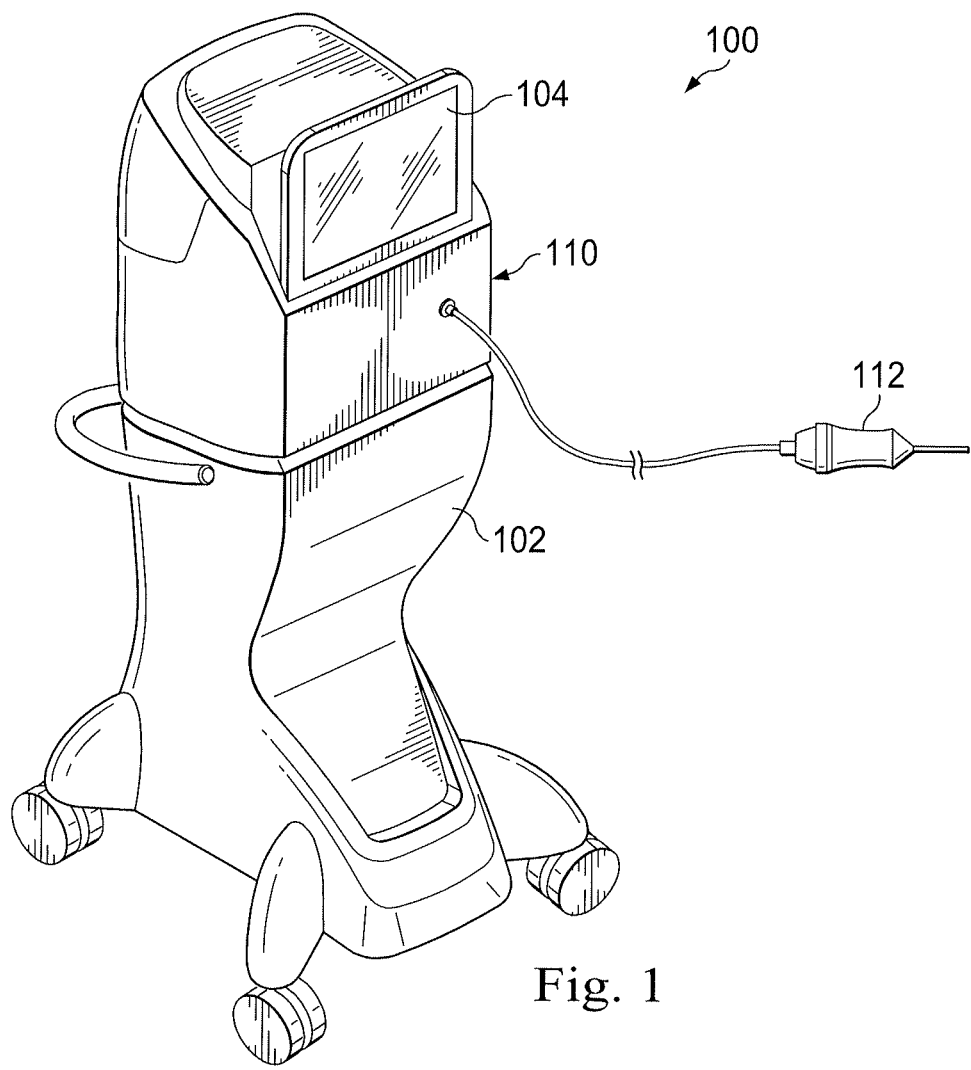
FIG. 1 is an illustration of an exemplary surgical system according to one aspect of the present disclosure consistent with the principles and teachings described herein.

For the purposes of promoting an understanding of the principles of the present disclosure, reference will now be made to the embodiments illustrated in the drawings, and specific language will be used to describe the same. It will nevertheless be understood that no limitation of the scope of the disclosure is intended. Any alterations and further modifications to the described systems, devices, and methods, and any further application of the principles of the present disclosure are fully contemplated as would normally occur to one skilled in the art to which the disclosure relates. In particular, it is fully contemplated that the systems, devices, and/or methods described with respect to one embodiment may be combined with the features, components, and/or steps described with respect to other embodiments of the present disclosure. For the sake of brevity, however, the numerous iterations of these combinations will not be described separately. For simplicity, in some instances the same reference numbers are used throughout the drawings to refer to the same or like parts.

The present disclosure is directed to surgical devices, systems, and methods for performing ophthalmic surgeries. The devices, systems, and methods operate or control cutting elements of a vitrectomy probe in manner providing a series of cuts followed by a brief break or recovery period. During these periodic recovery periods, the vitrectomy probe's aspiration port is closed. Periodically leaving the port closed may allow time for the vitreous fibers to relax and retract away from the vicinity of the aspiration port. This may reduce the probability of re-aspiration and a build-up in retinal traction.

In one aspect, this disclosure is directed to a change to the standard, continuous cutting operation of a vitrectomy probe. Instead of continuous cutting at a selected cut rate, the devices, systems, and methods disclosed herein include a cutting action having a number of cuts (burst) followed by a span of time where the port remains closed (delay or recovery period). In some examples, the length of the recovery period is a few cut cycles, such as between 1 and 5 cut cycles, although other lengths of recovery periods are contemplated.

FIG. 1 illustrates a vitrectomy surgical system, generally designated 100, according to an exemplary embodiment. The surgical system 100 includes a base housing 102 and an associated display screen 104 showing data relating to system operation and performance during a vitrectomy surgical procedure. The surgical system 100 includes a vitrectomy probe system 110 that includes a vitrectomy probe 112.

Figure 2:
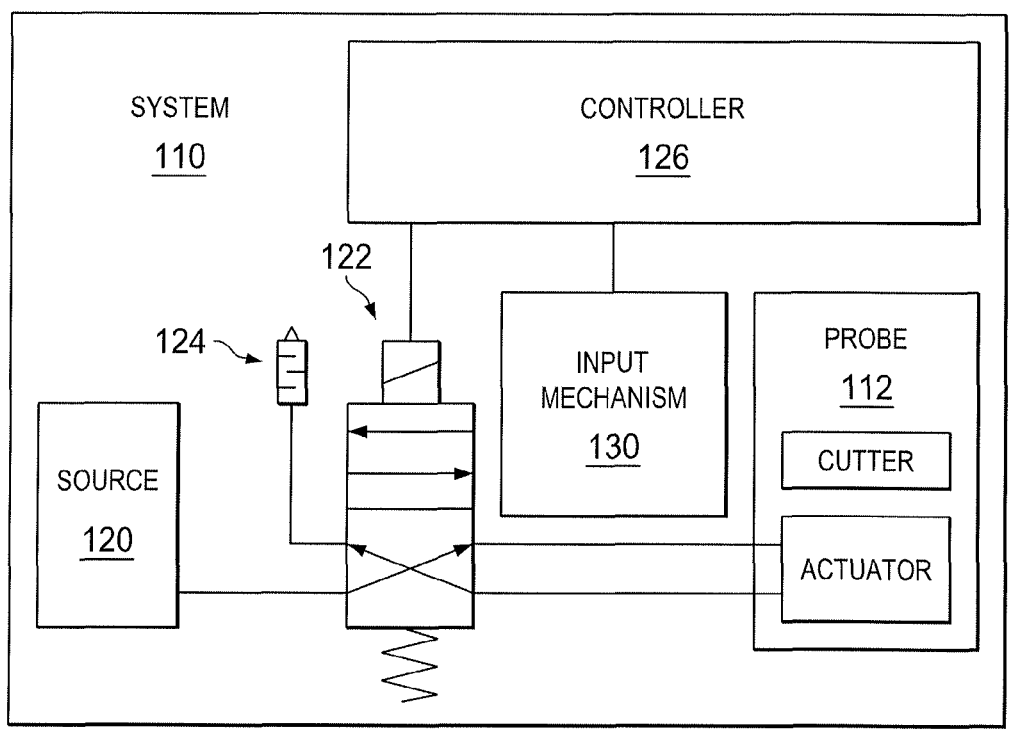
FIG. 2 is a block diagram of an aspect of the exemplary surgical system of FIG. 1 according to one aspect described herein.

FIG. 2 is a schematic of the vitrectomy probe system 110. The probe system 110 includes the vitrectomy probe 112, a pneumatic pressure source 120, a probe driver shown as an adjustable directional on-off pneumatic driver 122, a muffler 124, and a controller 126. As can be seen, the source 120, the driver 122, the muffler 124, and the probe 112 are in fluid communication with each other along lines representing flow paths or flow lines. The controller 126 is in electrical communication with the driver 122.

Figure 3:
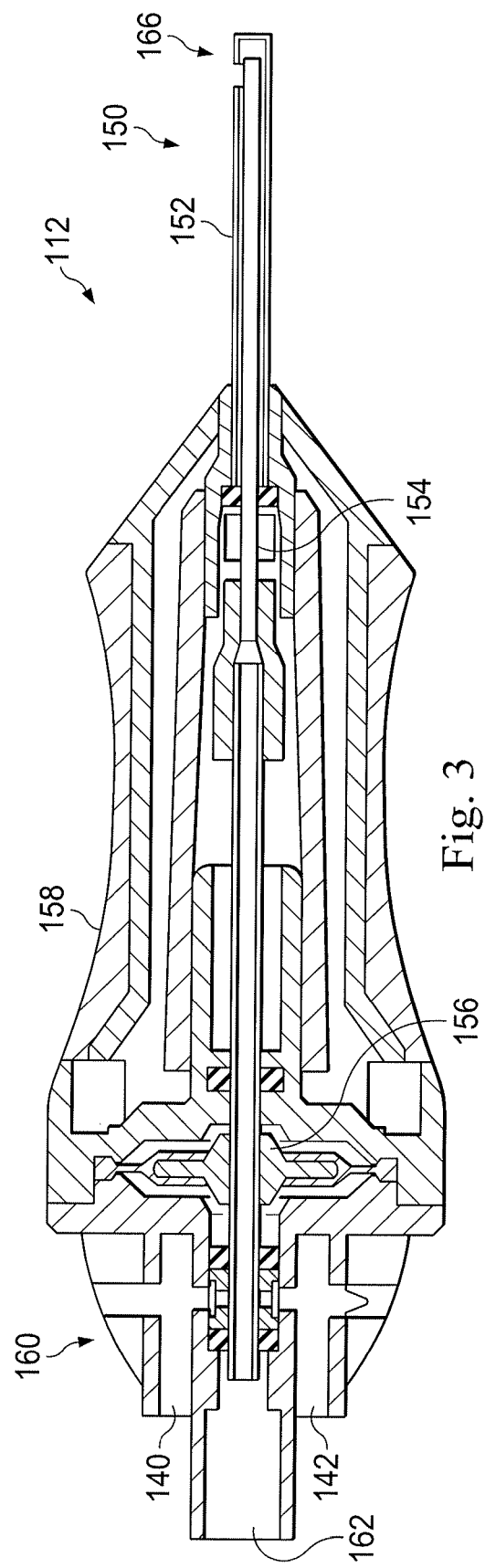
FIG. 3 is an illustration of an exemplary vitrectomy probe in cross-section operable in accordance with the principles and teachings described herein.

FIG. 3 shows a cross-sectional illustration of an exemplary vitrectomy probe, referenced by the numeral 112. In this example, the vitrectomy probe 112 is a pneumatically driven probe that operates by receiving pneumatic pressure alternating through first and second ports 140 and 142. The probe 112 includes as its basic components a cutter 150 comprising an outer cutting tube 152, an inner cutting tube 154, and a probe actuator shown here as a reciprocating air driven diaphragm 156, all partially encased by a housing 158. The housing 158 includes an end piece 160 at the probe proximal end with the first and second air supply ports 140, 142 and one suction port 162.

Figure 4:
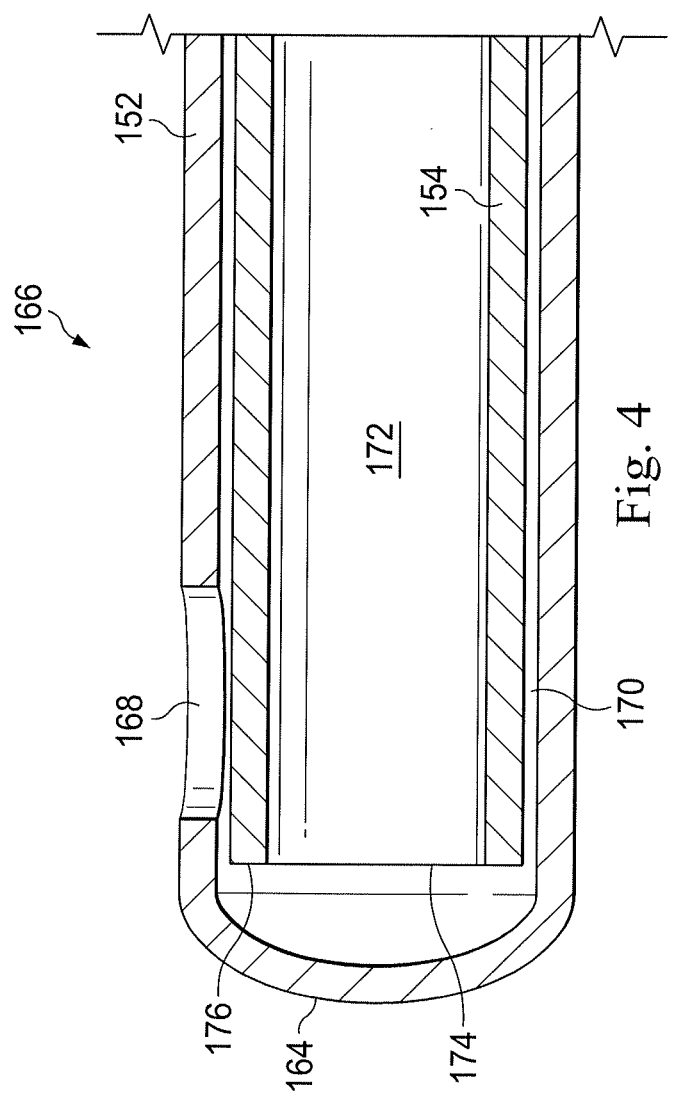
FIG. 4 is an illustration of an exemplary distal end of the vitrectomy probe in partial cross-section consistent with the principles and teachings described herein.

As can be seen, the cutter 150 extends from the housing 158 and includes a distal end 166. FIG. 4 shows the distal end 166 of the cutting tube 150 in greater detail. The cutter 150 includes the outer cutting tube 152 that has a closed end 164, and an outer port 168 that receives tissue, such as ophthalmic tissue. The outer port 168 is in fluid communication with an inner channel 170 of the outer cutting tube 152. The inner cutting tube 154 is located within the inner channel 170 of the outer cutting tube 152. The inner cutting tube 154 has an inner bore 172, an open end 174, and a cutting surface 176. The inner bore 172 is in fluid communication with an aspiration line (not shown) that connects to a vacuum pressure that pulls tissue into the outer port 168 when the inner cutting member 154 is located away from the port 168. The inner cutting tube 154 moves within the inner channel 170 of the outer cutting tube 152 to cut tissue that is pulled into the outer port 168 by the aspiration system. The ophthalmic tissue received by the outer port 168 is preferably vitreous or membranes.

When used to cut tissue, the inner cutting tube 154 is initially moved away from the outer port 168 and the vacuum pressure pulls tissue into the port 168 and the inner channel 172. The inner cutting tube 154 then moves toward the outer port 168 and severs the tissue within the inner channel 170. The severed tissue is pulled through the inner bore 172 of the inner cutting tube 154 by the aspiration system. The inner cutting tube 154 then moves away from the outer port 168, and the cutting process is repeated. A cutting cycle includes moving the inner cutting tube 154 to open the port 168 and then moving the cutting tube 154 to close the port 168 to initiate the cut and return the cutting tube 154 to its starting position for the next cutting cycle.

With reference now to both FIGS. 3 and 4, the inner cutting tube 154 is driven by air pressure directed on opposing sides of the diaphragm 156. In one example of operation, if air pressure is increased at the first port 140, the diaphragm 156 will move distally, displacing the inner cutting tube 154 relative to the outer cutting tube 152, thereby closing the tissue-receiving port 168 of the outer cutting tube 152. This cuts any vitreous material which may have been aspirated into the tissue-receiving outer port 168. Venting the pressure at the first port 140 and increasing the pressure at the second port 142 will move the diaphragm 156 proximally, opening the tissue-receiving outer port 168 so that it can draw in new vitreous material to be cut. It's worth noting that other embodiments include alternative probe actuators. For example, some actuator embodiments include a piston motor in place of a diaphragm. In this type of embodiment, the cutter 150 is arranged so that movement of the piston also moves the inner cutting tube 154 of the cutter 150. Yet other actuator embodiments include other types of pneumatic or electric motors that drive the inner cutting tube 154.

Returning to FIG. 2, in the example shown, the vitrectomy probe system's pneumatic driver 122 is a standard four-way on-off valve. As is commonly known, the pneumatic driver 122 has a solenoid that operates to move the driver to one of the two on-off positions depicted in the example of FIG. 2. Here, the pneumatic driver 122 is in a position to provide pneumatic pressure to the first port 140, and to vent pneumatic pressure from the second port 142. In this position, pneumatic pressure can pass from the pressure source 120, through the on-off pneumatic driver 122, and to the first port 140 where the pneumatic pressure provides pneumatic power to the vitrectomy probe. At the same time, pneumatic pressure at the second port 142 can pass through the on-off pneumatic driver 122 to the muffler 124 where it is exhausted to the atmosphere. In the other position, the on-off pneumatic driver 122 allows pneumatic pressure to pass from the pressure source 120 to the second port 142 where the pneumatic pressure provides pneumatic power to the vitrectomy probe 112. At the same time, pneumatic pressure at the first port 140 can vent through the on-off pneumatic driver 122 to the muffler 124 where it is exhausted to the atmosphere. The on-off pneumatic driver is configured to receive operating signals from the controller 126.

In operation, pneumatic pressure is directed alternately from the source 120 to the first and second ports 140, 142 (FIG. 3) to operate the vitrectomy probe 112. The on-off pneumatic driver 122 (FIG. 2) alternates between its two positions very rapidly to alternatingly provide pneumatic pressure to the first and second ports 140, 142.

Although shown with a single pneumatic driver 122, other embodiments include two pneumatic drivers, one associated with each of the two ports 140, 142. These embodiments operate similar to the manner described, with the drivers being configured to independently receive operating signals from the controller 126. Yet other arrangements are contemplated. In some embodiments, the pneumatic driver is replaced with or supplemented by a fluidic-driven valve. Yet other embodiments include piezo or voice coil actuation methods. Even other actuators types are contemplated.

Based upon control signals or inputs from an operator, the controller 126 can monitor and adjust the operation, such as whether to operate as a continuous mode or a burst mode. The controller may also receive and control the target cutting rate, the frequency of recovery periods, and other parameters.

The controller 126 comprises a processor and a memory and is configured to receive data, perform functions, and execute programs stored in the memory. In different embodiments, the controller 126 is, for example, a PID (Proportional-Integral-Derivative) controller, an integrated circuit configured to perform logic functions, or a microprocessor that performs logic functions. It may include a memory and a processor that may execute programs stored in the memory. In some embodiments, the memory stores fixed or variable cutting schemes and programs that may be retrieved or generated to correspond to desired cutting scenarios. Memory of the controller 126 is typically a semiconductor memory such as RAM (Random-Access Memory), FRAM (Ferroelectric Random-Access Memory), or flash memory. The memory interfaces with the processor. As such, the processor can write to and read from the memory. In this manner, a series of executable programs can be stored in the memory. The processor is also capable of performing other basic memory functions, such as erasing or overwriting the memory, detecting when the memory is full, and other common functions associated with managing semiconductor memory.

In addition, the system includes an input mechanism 130, such as a foot pedal, dial, knob, touch screen, sliding switch or other mechanism that allows a user to adjust the desired cut rate and mode of operation.

In one embodiment, the system includes at least two modes of operation, including a continuous cut mode and a burst mode. These modes may be selected by a user using the input device. In some embodiments, the system is configured to automatically elect or operate in the burst mode when cutting rates are selected above a preset threshold. For example, the system may be configured to operate in a continuous mode when cutting rates are below 10 k cuts per minute (cuts/min).

Figure 5:
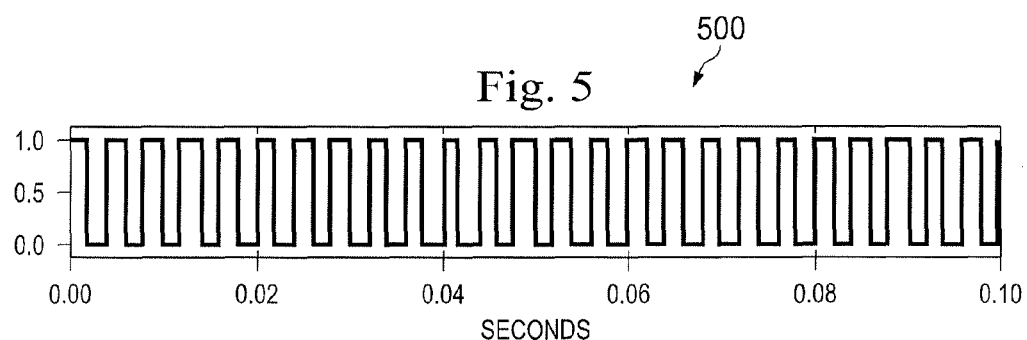
FIG. 5 is a graphical representation of a continuous mode cutting action by a vitrectomy probe consistent with the principles and teachings described herein.

In continuous cut mode, the system operates with at a continuous cutting rate that may be controlled by setting the cut rate to a certain level. A continuous cut mode cutting cycle is represented in the exemplary wave form 500 in FIG. 5. In this example, the cut rate is set, for ease of explanation at about 250 cuts per second, or 15000 cuts/minute. The wave form 500 represents the position of the inner cutting tube 154 in FIG. 4, relative to the port 168 in the outer cutting tube 152. Referring to the y-axis in FIG. 5, the "0" represents a closed port and the "1" represents a fully open port. Accordingly, the wave form 500 represents a continuous cutting rate in which the system generates control signals corresponding to a cutting scheme including a series of cuts evenly spaced in time that are not separated by a recovery period.

Figure 6:
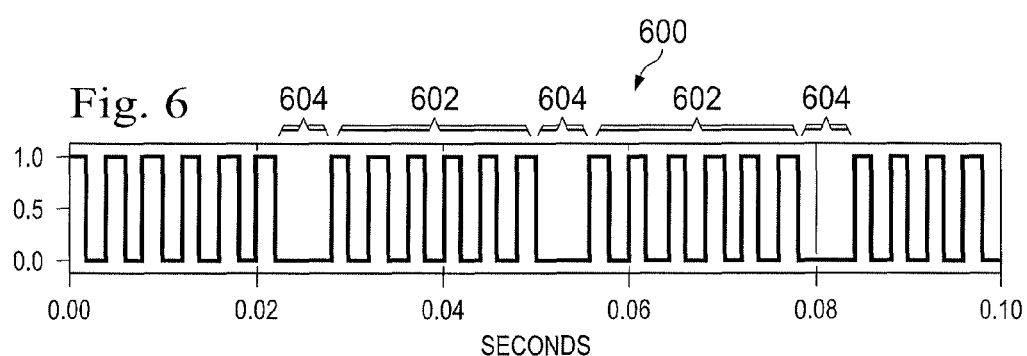
FIG. 6 is a graphical representation of a burst mode cutting action by a vitrectomy probe consistent with the principles and teachings described herein.

The burst mode cutting wave form is shown in FIG. 6, and identified by the reference numeral 600. This wave form is, in the example shown, also representing a 15000 cuts/minute rate. As can be seen, in this embodiment, one cycle period of every seven cycles is left with the port 168 closed. This is referenced to herein as a recovery period. Accordingly, the burst mode operation performs a series of cuts 602 at a particular cut rate, and then has a brief pause or recovery period 604, before performing the next series of cuts at the cut rate. As such, the system generates control signals corresponding to a cutting scheme including a plurality of series of cuts with each cut being evenly spaced in time, the plurality of series of cuts separated by a recovery period. In some embodiments, the system may control (e.g., vent or reduce) vacuum during the pause or recovery period to prevent/reduce a vacuum build-up.

The burst mode control may be achieved in different manners. For example, in one embodiment, the control scheme for the burst mode is a recovery period after a particular number or series of cuts. For example, the burst mode setting may generate a one cycle recovery period after every series of six cuts at a 15000 cut/min rate as shown in FIG. 6. Likewise, since the recovery period occurs after a preset number of cuts, the system also may generate a one cycle recovery period after every series of six cuts at an 18000 cut/min rate, or a one cycle recovery period after every series of six cuts at a 10000 cut/min rate. Accordingly, regardless of the cut rate, the recovery period occurs after a certain number of cuts.

Figure 7:
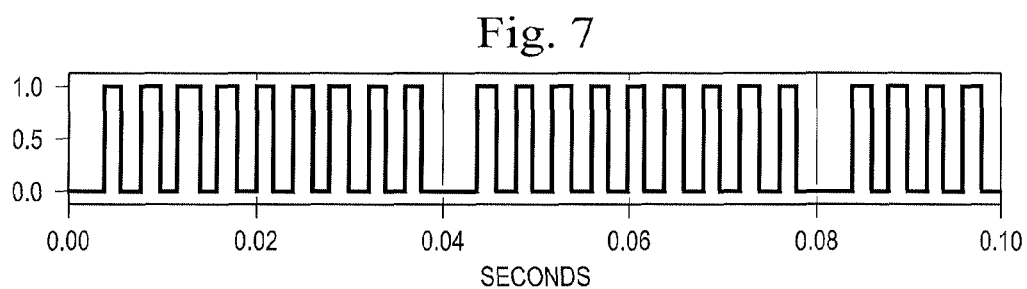
FIG. 7 is another graphical representation of a burst mode cutting action by a vitrectomy probe consistent with the principles and teachings described herein.
Figure 8:
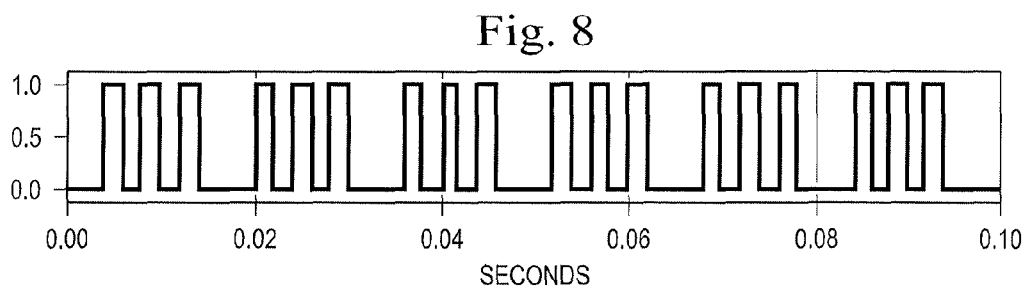
FIG. 8 is another graphical representation of a burst mode cutting action by a vitrectomy probe consistent with the principles and teachings described herein.

FIGS. 7 and 8 show alternative control schemes for the burst mode frequencies at the same 15000 cut/min rate. In FIG. 7, the recovery period is based on a time sequence, such that a recovery period occurs after a preset period of time, regardless of cutting speed. Accordingly, the number of cutting cycles between recovery periods varies depending on the cutting speed. For example, if the recovery periods are spaced 0.02 seconds apart, as shown in FIG. 7, the number of cuts between recovery periods at 20000 cuts/min will be double the number of cuts between recovery periods at 10000 cuts/min. In some examples, the controller is configured to initiate a recovery period within a range of about every 0.01 to 0.2 seconds during a cutting procedure. In some of these, the range is about every 0.03 to 0.2 seconds. Other ranges are contemplated.

FIG. 8 shows a recovery period occurring after every series of three cutting cycles. These same control schemes may be employed with any selected cut rate. In FIGS. 5-8, the length of the recovery period is set at about the same length of time as a single cutting cycle. However, other lengths of time may be used and are contemplated. In some examples, the length of the recovery period is dependent upon a selected cutting rate. In one example, the length of the recovery period is greater for a 15000 cuts/min rate than for a 10000 cuts/min rate.

Figure 9:
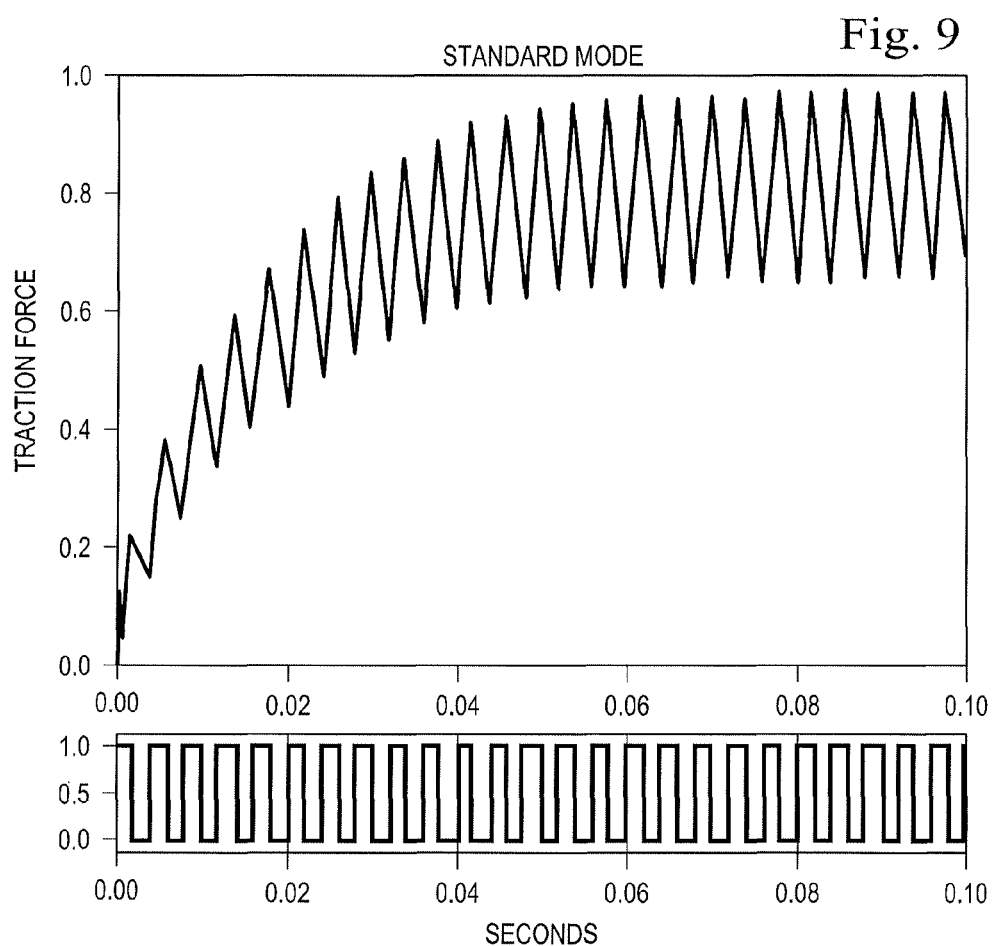
FIG. 9 is a graphical representation of a model showing vitreous traction forces resulting from a continuous mode cutting action by a vitrectomy probe consistent with the principles and teachings described herein.
Figure 10:
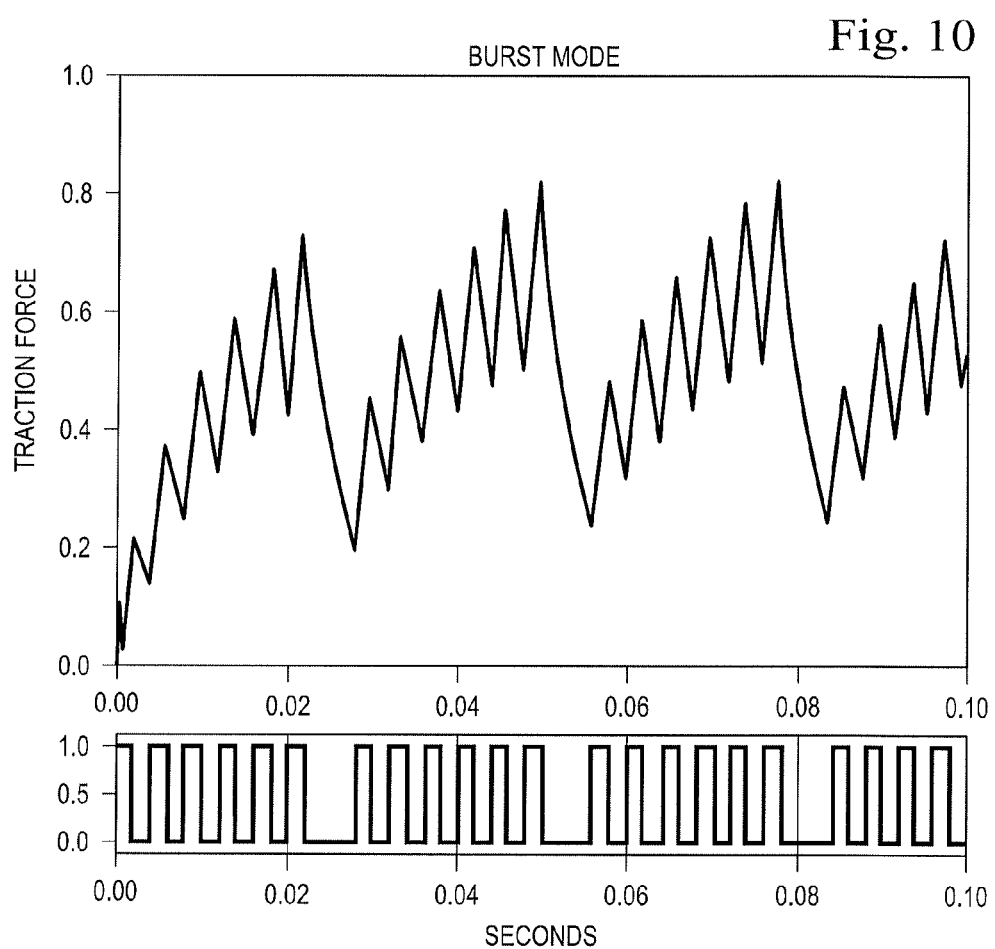
FIG. 10 is a graphical representation of a model showing vitreous traction forces resulting from a burst mode cutting action by a vitrectomy probe consistent with the principles and teachings described herein.

FIGS. 9 and 10 show simulated or estimated plots of vitreous traction over time during a vitrectomy procedure at 15000 cuts per minute. As can be seen by the plots, the traction does not return to zero between cuts. Instead, there is a residual traction that persists from cut to cut and an increase in peak tractions. The burst mode operation may reduce this build-up of traction.

FIG. 9 shows the simulated traction response when operating in continuous mode. FIG. 10 shows the simulated traction response when operating in burst mode. In each of these modes, the traction force is plotted relative to the individual cuts shown in the wave form below the traction plots. In the continuous mode of FIG. 9, during start-up vitreous traction persists and builds from an initial start until it plateaus at a running traction level. Accordingly, during the running period, the continuous mode has a traction level averaging about 0.8 units in the scale in FIGS. 9 and 10. In the burst mode of operation of FIG. 10, the traction force increases during start up, but permits traction to decrease during the recovery periods. As such, this may reduce the build-up of traction in the vitreous by allowing the vitreous fibers to have a chance to retract and withdraw from the field of influence at the port 168 (FIG. 4). The periodic recovery period may allow the vitreous fibers to relax and retract away from the vicinity of the aspiration port, potentially reducing the probability of re-aspiration and a build-up in traction. Accordingly, during the running period, the burst mode has a traction level averaging about 0.5 units in the scale in FIGS. 9 and 10. The lower traction forces, including an overall reduction in average traction forces, may lead to a decreased likelihood in retinal tears and retinal detachments.

Figure 11:
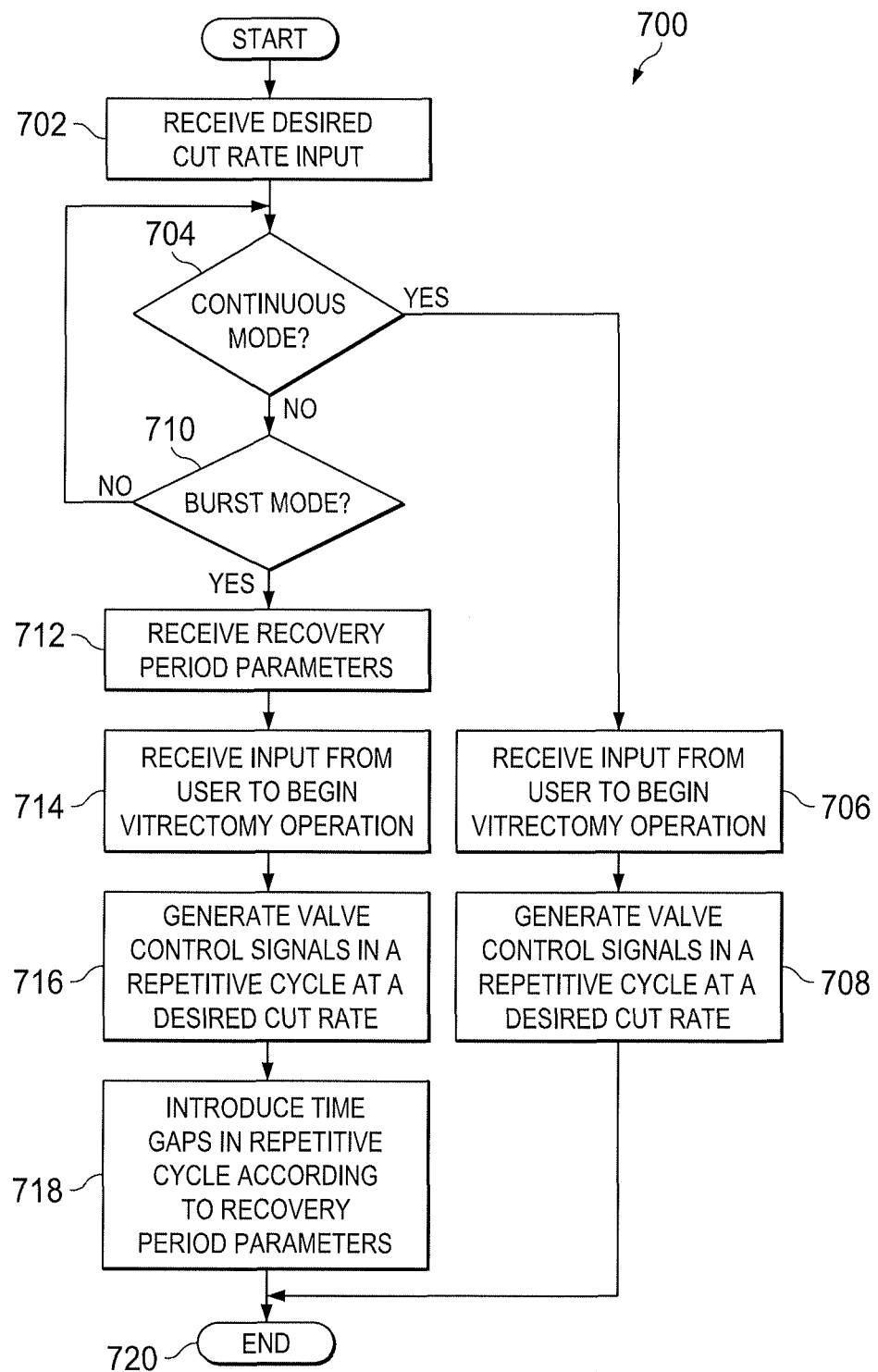
FIG. 11 is a flow chart showing an exemplary an operating method consistent with the principles and teachings described herein.

FIG. 11 shows an operating method 700 that may be used by the vitrectomy system to control the handpiece during a vitrectomy procedure. At 702, the system receives an input that indicates a desired cut rate. In one example, the input is received from a user, such as a surgeon. For example, the surgeon may select an input within a range of about 10000-25000 cuts/min. In another example, the desired cut rate input is received from the controller or pre-stored in the controller memory.

At 704, the controller 126 determines whether the system is operating in a continuous mode. The continuous mode relies on a cutting scheme where all cuts are substantially equally spaced apart in time to achieve the desired cut rate. At 706, the system receives an input from a surgeon to operate in order to begin a vitrectomy procedure. In some examples, this may occur via an input device such as a footpedal associated with the console of the surgical system. At 708, and in response to the input from the user, the controller 126 generates valve control signals in a repetitive cycle to operate the vitrectomy probe at the desired cut rate. The repetitive cycle means that the cut cycles are spaced apart in time by about the same amount. In embodiments employing electric actuation instead of fluidic actuation with a valve control signal, the controller 126 generates control signals in a repetitive cycle to operate the corresponding actuator at the desired cut rate.

At 704, if the system is not set to operate in continuous mode, then the system determines whether it is set to operate in burst mode at 710. As described above, burst mode is a mode where the repetitive cycle is interrupted with recovery periods that may permit vitreous fibrils to retract and withdraw from the aspiration port, potentially reducing traction. In this example, there are only two modes: continuous and burst. Therefore, if the system is not operating in burst mode at 710, the method returns to 704.

If the system is operating in burst mode at 710, then the system receives recovery period parameters at 712. The recovery period parameters may be received via an input at the console from the surgeon or may be stored in memory. In some embodiments, the parameters are stored within an executable program that also includes a complete vitrectomy program or scheme. The recovery period parameters may include information relating to the frequency and length of recovery periods within the vitrectomy cutting program. In one embodiment, the recovery period parameters correspond to length of recovery time after a particular number of cutting cycles. For example, the parameters may call for a recovery period to occur after every series of at least two cutting cycles, every series of at least four cutting cycles, every series of five cutting cycles, every series of six cutting cycles, or some other repeating scheme. In some embodiments, the parameters may call for a recovery period to occur after a series of cuts within a range of about 2 to 300 cuts. Other ranges and frequencies are contemplated.

In another embodiment, the recovery period parameters designate a recovery time to be initiated once or more for a specific period. For example, the parameters may call for a recovery period to occur every 0.02 seconds. Obviously, other frequencies and time periods may be used. In addition, although in FIGS. 6-8 each recovery period is the length of a single cutting cycle, the recovery period parameters may be longer or shorter than a single cutting cycle. In one example, the length of the recovery period is determined based on the amount of time it takes for the traction forces to fall beyond a threshold amount.

At 714, the system receives an input from a surgeon to operate in order to begin a vitrectomy procedure, as described above at 706. At 716, and in response to the input from the user, the controller 126 generates valve control signals in a repetitive cycle to operate the vitrectomy probe at the desired cut rate. In embodiments employing electric actuation instead of fluidic actuation, the controller 126 generates control signals in a repetitive cycle to operate the corresponding actuator at the desired cut rate.

At 718, the controller 126 introduces time gaps as recovery periods into the repetitive cycle according to the recovery period parameters. The method ends at 720.

The system disclosed herein, which uses intermittent gaps in cutting or recovery periods to maintain the access port 168 of the vitrectomy probe in a closed position for short periods, may permit vitreous fibers to retract from the aspiration port and may reduce traction and improve surgical result.

Persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

We claim:

1. A method comprising:
   receiving an input from a user to generate control signals to initiate a cutting action with a vitrectomy probe; and
   generating control signals corresponding to a patterned cutting scheme including both a) a plurality of series of cuts with each cut of the series of cuts being evenly spaced in time, and b) a recovery period separating each series of cuts of the plurality of series of cuts, wherein during the recovery period, a cutting port of the vitrectomy probe is closed to decrease traction on vitreous fibers between the series of cuts; and
   wherein the recovery period is a period of time equal to or greater than a single cutting cycle of one of the plurality of series of cuts.

2. The method of claim 1, comprising opening and closing a valve in accordance with the control signals to initiate the cutting with the vitrectomy probe.

3. The method of claim 1, further comprising selectively generating control signals corresponding to a second cutting scheme including a continuous series of cuts with each cut being evenly spaced in time.

4. The method of claim 1, wherein generating the control signals includes initiating the recovery period after a set number of cuts in a series, wherein the set number is input by the user.

5. The method of claim 1, wherein generating control signals corresponding to a patterned cutting scheme comprises initiating the recovery period every 0.01 to 0.20 seconds during the cutting scheme.

6. The method of claim 1, wherein a length of the recovery period is dependent upon the evenly spaced time period between the plurality of series of cuts in the patterned cutting scheme.

7. A method, comprising:
   receiving a first input from a user to implement a continuous patterned cutting scheme;
   opening and closing a cutting port on a vitrectomy probe according to the continuous patterned cutting scheme, wherein the continuous patterned cutting scheme consists of a first plurality of cuts with each cut being evenly spaced in time;
   receiving a second input from the user to switch to a burst patterned cutting scheme;
   opening and closing the cutting port on the vitrectomy probe according to the burst patterned cutting scheme, wherein the burst patterned cutting scheme comprises both a) a second plurality of series of cuts with each cut being evenly spaced in time, and b) a recovery period separating each series of cuts of the second plurality of series of cuts, wherein during the recovery period, the cutting port of the vitrectomy probe is closed, wherein the recovery period is a period of time equal to or greater than a single cutting cycle of one of the second plurality of series of cuts in the burst patterned cutting scheme.

8. The method of claim 7, wherein the burst patterned cutting scheme comprises initiating the recovery period every 0.01 to 0.20 seconds during the burst patterned cutting scheme.

9. The method of claim 7, wherein the burst patterned cutting scheme comprises initiating the recovery period after a set number of cuts in a series, wherein the set number is input by the user.

10. The method of claim 7, wherein receiving the first input from the user to implement the continuous patterned cutting scheme comprises receiving a user specified cut rate that is below a burst patterned cutting scheme cut rate and wherein receiving the second input from the user to implement the burst patterned cutting scheme comprises receiving a user specified cut rate that is above a burst patterned cutting scheme cut rate.

* * * * *